United States Patent [19]
Pawelek et al.

[11] Patent Number: 5,384,116
[45] Date of Patent: Jan. 24, 1995

[54] SYNTHETIC MELANIN AS A SUNSCREEN AND TANNING AGENT

[75] Inventors: John Pawelek; Michael P. Osber, both of Hamden, Conn.; Seth J. Orlow, Long Island City, N.Y.

[73] Assignee: Yale University, New Haven, Conn.

[21] Appl. No.: 16,418

[22] Filed: Mar. 25, 1993

Related U.S. Application Data

[60] Division of Ser. No. 867,851, Apr. 13, 1992, Pat. No. 5,227,459, which is a continuation-in-part of Ser. No. 674,489, Mar. 25, 1991, Pat. No. 5,225,435, which is a continuation of Ser. No. 603,111, Oct. 25, 1990, Pat. No. 5,218,079, which is a continuation of Ser. No. 525,944, May 18, 1990, Pat. No. 5,216,116.

[51] Int. Cl.$^6$ .............................................. C08G 63/06
[52] U.S. Cl. ....................................... 424/63; 424/59; 424/78.03; 514/415
[58] Field of Search ......................... 424/59, 63, 78.03; 514/415

[56] References Cited

U.S. PATENT DOCUMENTS

| | | | |
|---|---|---|---|
| 4,515,773 | 5/1985 | Herlihy | 424/59 |
| 4,968,497 | 11/1990 | Wolfram et al. | 424/59 |
| 5,017,194 | 5/1991 | Arifoglu et al. | 8/111 |

OTHER PUBLICATIONS

Orlow et al., 1992, "Synthesis and Characterization of Melanins from Dihydroxyindole-2-Carboxylic Acid and Dihydroxyindole," Pigment Cell Research 5:113–121.

Pawelek J. M., 1992, "Synthesis and Characterization of Melanins from Dihydroxyindole-2-Carboxylic Acid and Dihyroxyindole," in Pigment Cell Research, pp. 113–121.

Leonard et al., 1988, "Function of Dopachrome Oxidoreductase and Metal Ions in Dopachrome Conversion in the Eumelanin Pathway," Biochemistry 27:6156–6159.

Palumbo et al., 1987, "Effect of Metal Ions on the Rearrangement of Dopachrome," Biochemical et Biophysica Acta 925:203–209.

Korner and Gettins, 1985, "Synthesis in vitro of 5,6-Dihydroxyindole-2-Carboxylic Acid by Dopachrome Conversion Factor From Cloudman S91 Melanoma," Biological Abstracts 81(1):AB 601–602, Reference 5362.

Pawelek et al., 1982, "The Biosynthesis of Mammalian Melanin," American Scientist Mar.–Apr. 70(2):136–144.

Korner and Pawelek, 1981, "Dopachrome Conversion: A Possible Control Point in Melanin Biosynthesis," Biological Abstracts 71(1):389, Reference 3755.

Ito et al., 1974, "Isolation of Oligomers of 5,6-Dihydroxyindole-2-Carboxylic Acid From the Eye of the Catfish," Chem. J. 143:207–217.

*Primary Examiner*—Douglas W. Robinson
*Assistant Examiner*—Jean C. Witz
*Attorney, Agent, or Firm*—Pennie & Edmonds

[57] ABSTRACT

A melanin that is soluble in an aqueous solution at a pH between 5 and 9 at a temperature of 0° to 100° C. Advantageously, the melanin is capable of being filtered through at least a 0.45 micron size filter, and has a molecular weight of greater than 10,000 kilodaltons. The melanin is useful for providing a naturally-appearing tan to mammalian skin and hair. Such melanin can be produced by combining dopachrome and an appropriate enzyme, or by incubating 5,6-dihydroxyindole-2-carboxylic acid alone or with 5,6-dihydroxyindole, or with 3-amino-tyrosine. The melanin is also useful for providing a sun-screen to mammalian skin and hair, to treat post-inflammatory hypo- and hyperpigmentation, to tint glass and plastic, to protect industrial materials against ultraviolet damage, and as a coloring agent in foodstuffs such as coffee, tea, soda, whiskey and liquors.

4 Claims, 10 Drawing Sheets

SYNTHETIC MELANIN AS A SUNSCREEN AND TANNING AGENT

This application is a division of application Ser. No. 07/867,851 filed Apr. 13, 1992, now U.S. Pat. No. 5,227,459 which is a continuation-in-part of Ser. No. 07/674,489 filed Mar. 25, 1991, now U.S. Pat. No. 5,225,435 which in turn is a continuation of Ser. No. 07/603,111 filed Oct. 25, 1990, now U.S. Pat. No. 5,218,079 which in turn is a continuation of Ser. No. 07/525,944 filed May 18, 1990, now U.S. Pat. No. 5,216,116.

FIELD OF THE INVENTION

The present invention concerns the synthesis of soluble forms of melanin and their composition, and methods of using such compositions to provide a natural-appearing tan to mammalian skin and hair and to provide a sun-screen, to treat hypopigmentation, to tint glass and plastic, to provide color to foods and beverages, and to protect industrial materials against ultraviolet damage.

BACKGROUND INFORMATION

In biology, melanins are heteropolymers consisting of L-dopa and its enzymatic derivatives. They are ubiquitous in living organisms and are produced throughout the zoological and botanical phyla. In mammalian skin, melanins are produced through enzymatic processes in specialized cells known as "melanocytes". Melanins are the pigments of mammalian skin and hair.

Mammalian melanins are highly insoluble and can be dissolved (solubilized) only through non-physiological treatments such as boiling in strong alkali, or through the use of strong oxidants such as hydrogen peroxide. Tyrosinase, a key enzyme in the melanin biosynthetic pathway, can catalyze the formation of melanin in a test tube using L-tyrosine, L-dopa or 5,6-dihydroxyindole as substrates; however, the product is an insoluble precipitate as described above.

Ito, "Reexamination of the Structure of Eumelanin", *Biochimica et Biophysica Acta*, 833, 155–161, 1986, mentions that natural melanin may be a polymer of 5,6-dihydroxyindole and 5,6-dihydroxyindole-2-carboxylic acid. Ito, however, does not teach or suggest combining these chemicals to form melanin.

Ito and Nicol, "Isolation of Oligimers of 5,6-Dihydroxyindole-2-carboxylic Acid from the Eye of the Catfish", *Biochemical Journal*, 143, 207–217, 1974, mention that oligimers of 5,6-dihydroxyindole-2-carboxylic acid exist in nature, for example in the tapetum lucidum of the sea catfish (*Arius felis*). Ito and Nicol, however do not teach or suggest that these structures could be used as a form of soluble melanin.

Palumbo, d'Ischia, Misuraca, and Prota, "Effect of metal ion on the rearrangement of dopachrome", *Biochimica et Biophysica Acta*, 925, 203–209, 1987, mention that the non-decarboxylative rearrangement of dopachrome at physiological pH values, leading mainly to the formation of 5,6-dihydroxyindole-2-carboxylic acid. They suggest that when considered in the light of the known metal accumulation in pigmented tissues, their results provide a new entry into the regulatory mechanisms involved in the biosynthesis of melanin. Palumbo et al., however, do not teach or suggest that such metal ions could be used to affect the color or formation of soluble melanin. Likewise, Leonard, Townsend, and King, "Function of Dopachrome Oxidoreductase and Metal Ions in Dopachrome Conversion in the Eumelanin Pathway", *Biochemistry*, 27, 6156–6159, 1988, present similar results to those of Palumbo et al. regarding metal ions and the formation of 5,6-dihydroxyindole-2-carboxylic acid from dopachrome. Like Palumbo et al., Leonard et al. also do not teach or suggest that such metal ions could be used to affect the color for formation of soluble melanin.

Korner and Pawelek, *J. Invest Dermatol.* 75, 192–195, 1980, report the presence of an enzymic activity, "dopachrome conversion factor", in melanocytes which catalyzes the conversion of dopachrome to 5,6-dihydroxyindole-2-carboxylic acid. Pawelek, *Biochem. Biophys. Res. Comm.*, 166, 1328–1333, 1990, showed that this conversion reaction is an isomerization and that dopachrome conversion factor is an isomerase. Aroca, Garcia-Borron, Solano, and Lozano, *Biochem. Biophys. Res. Acta*, 1035, 266–275, 1990, suggested that the mechanism is indeed an isomerization which involves a tautomeric shift and proposed that the enzyme be named "dopachrome tautomerase" with the official Enzyme Commission number of E.C.5.3.2.3. Tsukamoto, Jackson, Urabe, Motague, and Hearing, *EMBO J.*, in press, 1992, reported identification of a gene for dopachrome tautomerase. The above information is reviewed by Pawelek, *Pigment Cell Research*, 4, 53–62, 1991.

Wolfram et al. (U.S. Pat. No. 4,968,497) disclose tanning by applying a composition comprising melanin precursors or melanin precursor-like materials to the skin. They do not teach or claim that applying melanins, either natural or synthetic, to the skin will mimic skin tanning. Rather they teach that such melanins achieve "only superficial external tanning results which is readily removed by rinsing with water or rubbing with a towel".

Herlihy (U.S. Pat. No. 4,515,773) discloses a skin tanning composition containing a melanin precursor and a tyrosinase enzyme in a cosmetic base. He does not, however, teach or claim the application of melanins, either natural or synthetic to the skin.

Gaskin (U.S. Pat. No. 4,806,344) discloses a sun protectant composition comprising "melanin" as one of the ingredients. Gaskin further discloses that the melanin is "synthesized from tyrosinase and DOPA". She does not teach or suggest that such melanin is synthesized non-enzymatically or that it is comprised of precursors which confer either negative or positive charges on the polymer, rendering it soluble in aqueous solutions.

Many reports exist exploring the role of sulfhydryl compounds such as cysteine or glutathione in determining the red or yellow colors in melanin (see review by Prota, d'Ischia, and Napolitano, "The Regulatory Role of Sulfhydryl Compounds in Melanogenesis", *Pigment Cell Research, Supplement* 1, 48–53, 1988. However, these reports do not teach or suggest that said sulfhydryl compounds could be used to influence the colors of synthetic soluble melanins.

It would be of commercial value to have synthetic varieties of melanin with different solubility, molecular size, and color characteristics. That is, it would be useful to be able to produce various melanins of predictable colors and physicochemical characteristics through specific changes in the synthetic reaction conditions. For example, it would be of value to produce a melanin that, at neutral pH, is soluble in aqueous solvents such as those used in skin creams and lotions, while at acid pH, is soluble in organic solvents such as those used in oil-based paints.

Such melanins could impart a natural-appearing tan to mammalian skin and hair. Such melanins would also be effective as sun-screens, since melanins are the chemicals in the skin which absorb ultraviolet radiation and thus provide protection from its harmful effects, such as premature skin aging and the occurrence of skin cancers.

Such melanins would be effective in treating post-inflammatory hypopigmentation due to eczema, acne, trauma, burns and psoriasis. Also as a cover-up for vitiligo and other disorders of hypopigmentation, soluble melanins would be quite effective.

Since melanins absorb light throughout the ultraviolet and visible spectra, they would also be effective as glass or plastic tinting agents for eye glasses, contact lenses, car windows, house windows, office buildings, etc. Since melanins exhibit brown, red-brown, and golden-brown colors, they would be effective food and beverage colorants for such things as beer, tea, coffee, potato chips, and the like.

Likewise, by absorbing in the ultraviolet range, such melanins would be effective agents in protecting industrial materials against damage from ultraviolet radiation. By "industrial material" or "industrial product" is meant, for example, truck and car tiers, paints, laminating materials, plastics, synthetic resins, and fabrics, particularly fabrics containing nylon, and like materials or products. It is well known that the rate of deterioration of paints, wood, plastics and rubber is dramatically increased by exposure to ultraviolet radiation.

In application Ser. No. 674,489, filed Mar. 25, 1991, now pending, and in its parent applications, Ser. No. 603,111 filed Oct. 25, 1990, now pending, and Ser. No. 525,944 filed May 18, 1990, now pending, there are disclosed novel soluble melanins and processes for their production.

One such process involves reaction of dopachrome with at least one enzyme, now known as dopachrome tautomerase, derived from biological cells or tissues which contain a pigmentary system. Advantageously, 5,6-dihydroxyindole, indole-5,6-quinone and/or melanochrome are also present.

If 5,6-dihydroxyindole-2-carboxylic acid is included in the reaction system, dopachrome and dopachrome tautomerase may be omitted and a soluble melanin will still be produced.

While the resulting soluble melanins are quite satisfactory in performance, there are certain limitations in their solubility over a broad pH range. Moreover, the colors of the soluble melanins are somewhat limited in scope.

SUMMARY OF THE INVENTION

It is accordingly an object of the present invention to provide additional synthetic forms of soluble melanin at physiological pH and temperatures.

It is another object of the present invention to provide compositions and methods for modifying the spectral characteristics of such melanins.

It is another object of the present invention to provide compositions and methods for modifying the solubility characteristics of such melanins so that they can be dissolved readily in either organic or aqueous solvents.

It is another object of the present invention to provide compositions and methods for increasing the adherence of such melanins to mammalian skin and hair.

It is another object of the present invention to provide compositions and methods for applying such melanins to mammalian skin and hair to provide a natural-appearing tan.

It is another object of the present invention to provide compositions and methods for applying such melanins to mammalian skin and hair to provide a sunscreen.

It is another object of the present invention to provide compositions and methods of applying such melanins to skin to treat hypopigmentation.

It is another object of the present invention to provide compositions and methods for applying such melanins to glass and plastic to provide tint.

It is another object of the present invention to provide compositions and methods for applying such melanins to industrial products to provide protection against ultraviolet radiation.

It is another object of the invention to provide coloring agents based on soluble melanin to foodstuffs such as coffee, tea, soda, beer, whiskey, liquor, potato chips, and the like.

It is yet another object of the invention to provide soluble melanins which retain their solubility over a wide pH range.

Still another object is to provide soluble melanins with an array of possible colors.

The above objects and other objects, aims, and advantages are satisfied by the present invention. The present invention relates to a melanin that is soluble in aqueous solution, e.g., water or an aqueous buffered solution, at a pH of at least 5 to 9, preferably 6.5 to 7.5, at a temperature of 0° to 100° C. The present invention also relates to a melanin that is soluble in organic solutions, e.g., butanol or butoxyethanol. The soluble melanin is further characterized by being capable of being filtered through at least a 0.45 micron size filter. The solubility of the melanin in aqueous solutions around neutral pH is in large part due to the abundance of carboxyl and/or amino-groups, whereas the solubility of the melanin in organic solutions is in large part due to the protonation of said carboxyl-groups at acid pH, and/or the de-protonation of amino-groups at basic pH.

The present invention also concerns a method of producing synthetic melanin comprising combining in a reaction mixture dopachrome and dopachrome tautomerase and a phenethylamine of the formula in which
X and Y each independently is OH or $NH_2$,
R is H or COOH,
$R_1$, $R_2$ and $R_3$ each independently is H, $NO_2$, CHO, CN, $OR_4$, halogen, $NR_5R_6$, $COOR_7$, $SR_8$, $OPO_3H$, $OSO_2H$ or $OOCCH_3$, and
$R_4$, $R_5$, $R_6$, $R_7$, and $R_8$ each independently is H or alkyl, preferably lower alkyl of 1 to 4 of 1 to 4 carbon atoms.

A preferred phenethylanine is 3-amino-tyrosine which imparts a red golden cast to the resulting melanin.

A 5,6-dihydroxyindole and/or 3-amino-tyrosine may be added to the dopachrome and the enzyme dopachrome tautomerase, or dopachrome may be allowed to spontaneously form 5,6-dihydroxyindole before adding the enzyme. Alternatively, the reaction mixture may comprise a 5,6-dihydroxyindole-2-carboxylic acid alone, or in a mixture with 5,6-dihydroxyindole and/or 3-amino-tyrosine, or the reaction mixture may comprise a 5,6-dihydroxyindole in combination with 3-amino-tyrosine, in which cases enzymes are not necessary and the reactions occur in the presence of oxygen. The rates of reactions are greatly enhanced by the additions of hydrogen peroxide and/or salts of metal ions, e.g., salts of $Cu^{2+}$ or $Fe^{2+}$.

Suitable 5,6-dihydroxyindole-2-carboxylic acids are the formula particularly 5,6-dihydroxyindole-2-carboxylic acid, i.e. the compound in which X and Y are OH and $R_1$ and $R_2$ are hydrogen.

The color of the soluble melanin can be varied between black, brown, red and yellow by altering the contents of the reaction mixtures, for example by adding sulfhydryl containing compounds, or various metals such as, but not limited to, $Cu^{2+}$, $Ni^{2+}$, and $Co^{2+}$ or by altering the pH of the reaction mixtures.

The basis for the solubility of the melanin in aqueous solutions is in a large part due to the high degree of carboxyl groups present in the molecule, said carboxyl groups being incorporated as part of the 5,6-dihydroxyindole-2-carboxylic acid precursor. When 3-amino-tyrosine or similar compounds are incorporated into the melanin, the basis for the solubility of the melanin is also due to the high degree of amino groups present in the molecule, said amino groups being incorporated as part of the 3-amino-tyrosine precursor. Compounds similar to 5,6-dihydroxyindole-2-carboxylic acid or 3-amino-tyrosine could substitute in providing said carboxyl- or amino groups and could therefore also act as precursors to soluble melanin.

DETAILED DESCRIPTION OF THE INVENTION

The melanins of the invention remain in aqueous solution, at neutral pH (e.g., pH of 5 to 9, preferably 6.5 to 7.5), for long periods of time, e.g., indefinitely, at room temperatures of 0° C. to 100° C., e.g., room temperature. The melanins according to the invention are further characterized by remaining soluble upon freezing/thawing. The inventive melanins are also characterized by being capable of being filtered through at least a 0.45 micron size filter. The melanins according to the invention can be precipitated below pH 4.

Following synthesis, the melanins cannot be dialyzed through a semi-permeable membrane which allows the passage of molecules having less than a molecular weight of approximately 10,000. Therefore the melanins according to the invention are of molecular weights greater than 10,000; however, this is not an essential characteristic for their usefulness. The melanins can be lyophilized to a dry powder form and then reconstituted to soluble form with distilled water or suitable aqueous solvents, e.g., sodium phosphate 0.1M or sodium chloride 0.1M. Following precipitation at acid pH, they can also be reconstituted in organic solvents such as butanol or 2-butoxyethanol.

The melanins according to the invention can be prepared non-enzymatically (synthetically) or enzymatically.

The enzymatic preparation according to the invention comprises combining in a reaction mixture a substrate, i.e., dopachrome and dopachrome tautomerase (E.C.5.3.2.3) which catalyzes the isomeric tautomerization of dopachrome to 5,6-dihydroxyindole-2-carboxylic acid (DHICA).

In the non-enzymatic preparation according to the invention, the reaction mixture comprises as a substrate DHICA alone or a mixture of DHICA, 5,6-dihydroxyindole, and/or 3-amino-tyrosine. Suitable analogs of DHICA, i.e., similar structures containing carboxyl- or amino- groups, may be substituted in the reaction. Likewise, similar structures containing other electrically charged moieties, such as phosphate groups may be substituted in the reaction. An example of such a structure is 3'- and/or 4'- phosphoryl phenylalanine (dopa phosphate). The enzymatic or nonenzymatic reaction mixtures may still further comprise as a substrate indole-5,6-quinone and/or melanochrome. Metal ions and sulfhydryl-containing compounds may be included.

The individual components of the substrate, be it one component, i.e., dopachrome, as in the enzymatic preparation, or more than one component as in the nonenzymatic preparation, preferably will be in an amount of 0.01 to 5.0 millimolar, but not necessarily limited to this concentration range.

The combining of substrate and enzymes, or precursors without enzymes in the reaction mixtures is preferably conducted at a temperature of 15° C. to 90° C.

It is preferred in both the enzymatic and nonenzymatic preparation that oxygen, e.g., air or pure oxygen, be present. This is especially true for the nonenzymatic preparations.

Structural formulas and the relationship among some of the above described compounds are depicted as follows:

Scheme I

Scheme II

Scheme II 5,6-dihydroxyindole
(DHI)

5,6-dihydroxyindole-2-carboxylic acid
(DHICA)

From Scheme I it is seen that dopa quinone, leuco dopachrome, dopachrome, DHICA, 5,6-dihydroxyindole, indole-5,6-quinone, and melanochrome are all derivatives of dopa. Dopa itself is a derivative of tyrosine, so the above compounds are also derivatives of tyrosine.

Scheme II shows that dopachrome can give rise to 5,6-dihydroxyindole in a spontaneous non-enzymatic reaction, or it can give rise to DHICA in an enzymatically-catalyzed reaction. Dopachrome can also give rise to DHICA in a metal-catalyzed reaction (not shown). The enzyme which catalyzes dopachrome to DHICA is named dopachrome tautomerase. The enzyme may also be a part of a complex comprising tyrosinase, dopachrome tautomerase, glycoprotein 75, MSH receptor, lysosome-associated membrane protein-1 and other unknown proteins.

The above described enzymes are described in the following papers:
  tyrosinase: Ann Korner and John Pawelek, "Mammalian Tyrosinase Catalyzes Three Reactions in the Biosynthesis of Melanin", *Science*, 217:1163-1165, 1982;
  dopachrome tautomerase: John Pawelek, "After Dopachrome?", *Pigment Cell Research*, 4:53-62, 1991.
  glycoprotein 75: Timothy M. Thomson, M. Jules Mattes, Linda Roux, Lloyd Old and Kenneth O. Lloyd, "Pigmentation-associated Glycoprotein of Human Melanomas and Melanocytes: Definition with a Mouse Monoclonal Antibody", *J. Invest. Derm.*, 85:169-174, 1985;
  MSH receptor: Seth J. Orlow, Sara Hotchkiss, and John M. Pawelek, "Internal Binding Sites for MSH: Analyses in Wild Type and Variant Cloudman Melanoma Cells:, *J. Cellular Physiology*, 142:129 136, 1990.

The melanins according to the present invention can be admixed with a physiologically acceptable carrier to form a composition, which has the uses previously noted.

Physiologically acceptable carriers useful in the practice of the invention are known in the art and non-limiting examples of such carriers include, for controlled release—microcapsules comprising carboxymethylene copolymers; for transdermal release—acrylamides; and for topical application—cosmetic bases.

In addition, if desired, the composition according to this embodiment comprises at lease one additive selected from the group consisting of solvents, fragrances, sunscreening agents, preservatives and chelating agents.

Cosmetic bases useful in the practice of the invention are well known and include lotions, creams, ointments, lipstick, blush, cover-up, foundations and dusting powders. Examples thereof may be found in, e.g., U.S. Pat. Nos. 4,228,151; 4,282,206 and 2,949,403.

In the case that the inventive compositions are used as tinting agents for glass and plastic or as industrial product protecting agents, e.g., for protection against UV degradation, the inventive composition will be incorporated into the glass or plastic or industrial product. Simply by virtue of their soluble nature, the inventive compositions are easily incorporated in the glass or plastic or industrial product. For such uses the carriers, diluents, or the like, would not have to be physiologically acceptable. Other conventional agents for such uses could also be formulated therewith.

Solvents for use in accordance with the invention include, for example, ethanol, isopropyl alcohol, benzyl alcohol, oil, for example, ground nut oil, distilled and/or deionized water, physiological saline solution and the like. The specific solvent chosen will depend on the method of application.

It may also be desirable to add a preservative to the inventive compositions if they are to be used for topical applications. The preferred mode of administration of the inventive compositions is topical administration. Still further, the melanins of the present invention may be combined with substances that stimulate the pigmentary system under conditions of low levels of UV light.

Preservatives are well known and may be exemplified by methylparaben, "DOWACIL 2000" and propylparaben.

If desired, in order to reduce the acidity or basicity of the inventive compositions, bases, acids or buffers may be added thereto in accordance with the knowledge of the art.

The concentration of melanins in an aerosol, cream, lotion or other composition is preferably 1.0 mg/ml to 100 mg/ml, but not restricted to this concentration range.

Solutions have different colors depending on the concentration of "chromophore" dissolved in them. For example, a deep red solution will appear orange or pink when diluted with more solvent, but no additional chromophore. In the case of the soluble melanin, when it is dissolved at a fairly high concentration in water, e.g., 0.5 mg/ml, it appears brown-black in color. When more water is added so that the concentration of the soluble melanin is reduced to, e.g., 0.1 mg/ml, the solution appears golden in color. It is not believed that diluting the material effects any shift in the absorbance spectrum, rather it is believed to be a visual perception.

For the nonenzymatic preparation, the 5,6-dihydroxyindole-2-carboxylic acid, 5,6-dihydroxyindole, and 3-amino-tyrosine may be maintained separately, for example, in microspheres, or in separate tubes or containers, until being mixed together on the skin of a mammal, e.g., human.

Figure 7:
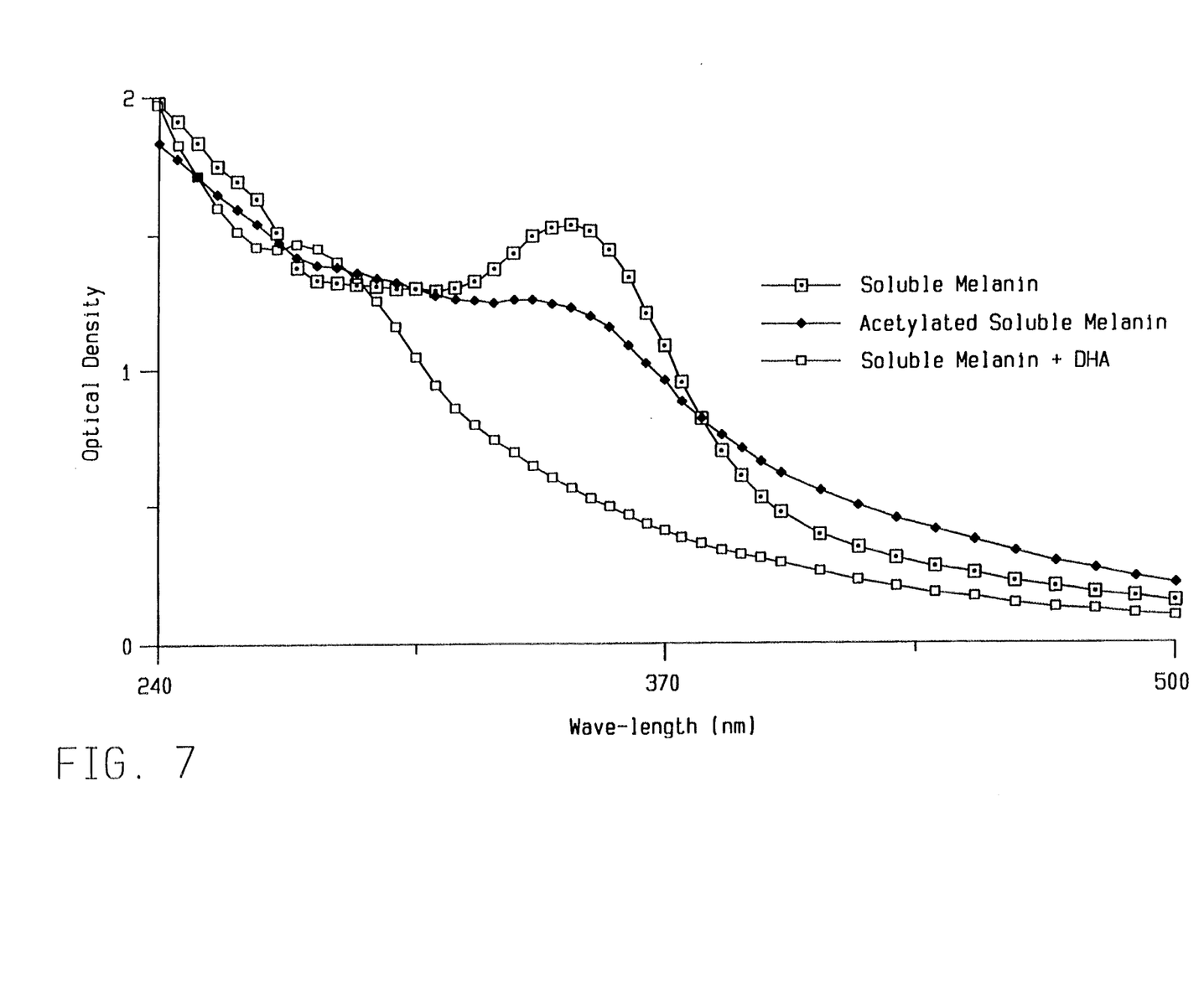
FIG. 7 depicts a graph showing the spectral characteristics of soluble melanin composed of a mixture of DHICA (10%) and 3-amino-tyrosine (90%).

The melanins can be made to adhere to the skin for several days and be resistant to water and soap simply by mixing the melanin with any commercially available preparation of dihydroxyacetone (DHA), e.g., Lancome's Conque le du Sol oil ®. The DHA apparently acts as a cross-linking agent to covalently link the melanin with various factors, e.g., proteins in the skin. It is likely that other cross-linking agents will achieve the same or better results. An additional advantage of treatment with DHA is that such treatment alters the spectral characteristics of the melanin, giving it a more even absorbance throughout the UV and visible spectra, without substantially altering the color of the melanin. Treatment of melanins with acetic anhydride also alters the spectral characteristics of the melanin (FIG. 7).

DETAILED DESCRIPTION OF THE DRAWINGS

Figure 1:
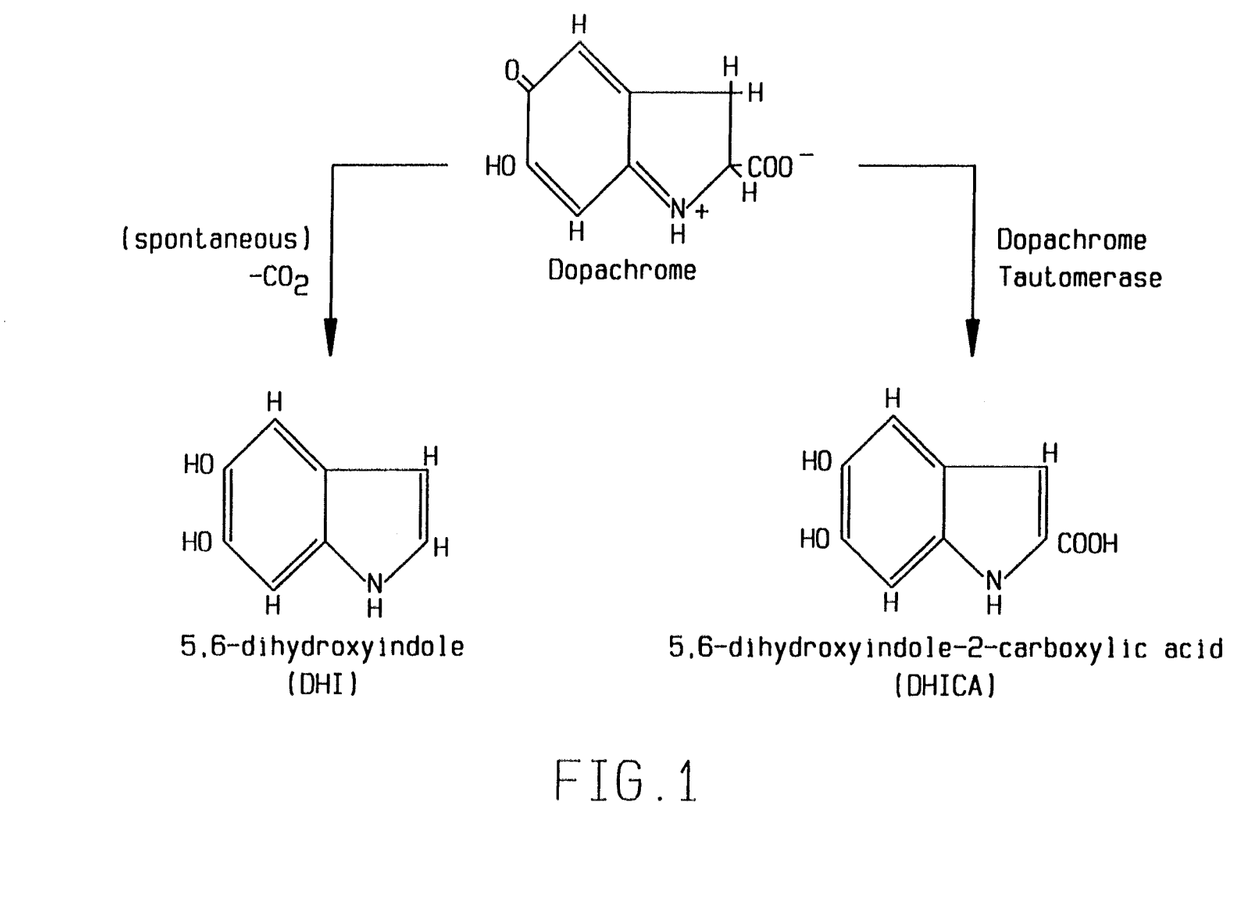
FIG. 1 depicts a schematic representation of two pathways for the metabolism of dopachrome.

Referring now more specifically to the drawings:

FIG. 1 depicts a schematic representation of two pathways for the metabolism of dopachrome. In a test tube, dopachrome spontaneously converts to dihydroxyindole (DHI), losing its carboxyl group in the process, however if the enzyme dopachrome tautomerase is present, dopachrome is converted to 5,6-dihydroxyindole-2-carboxylic acid (DHICA).

Figure 2A:
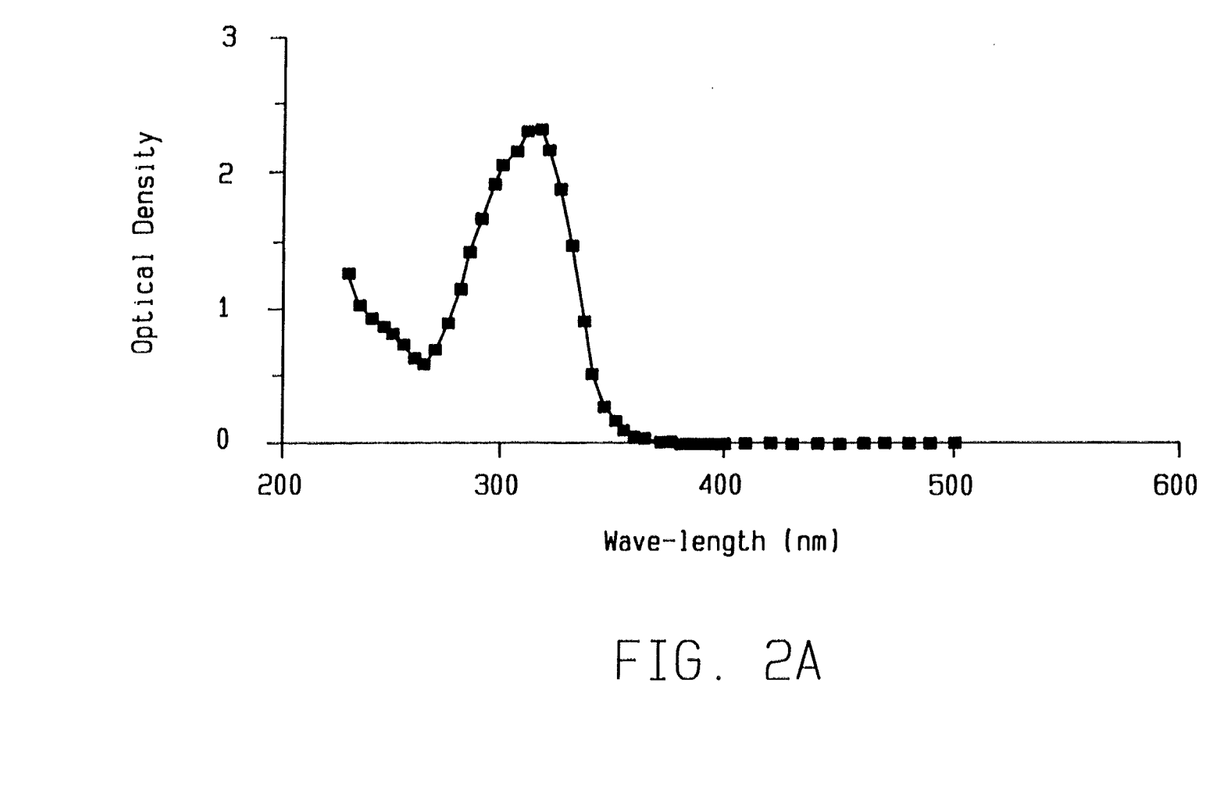
FIG. 2A-C depict graphs showing spectral analyses of DHICA (5 mM) incubated with oxygenation for various time periods in sodium phosphate buffer (0.1M, pH 7.8, 20° C.), compared to that of the product of the dopachrome tautomerase reaction (incubation of enzyme+dopachrome 5 mM) (2D).
Figure 2B:
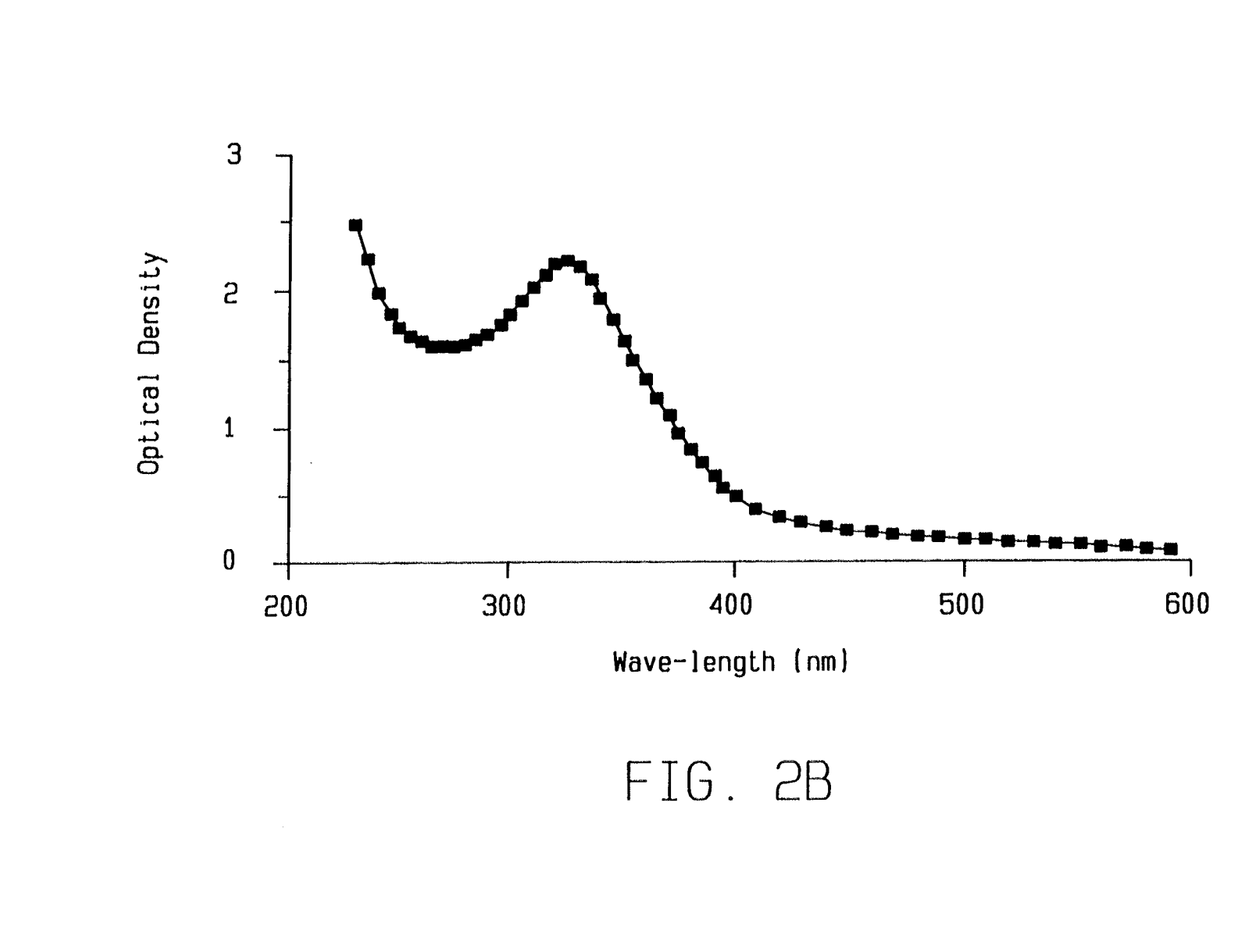
Figure 2C:
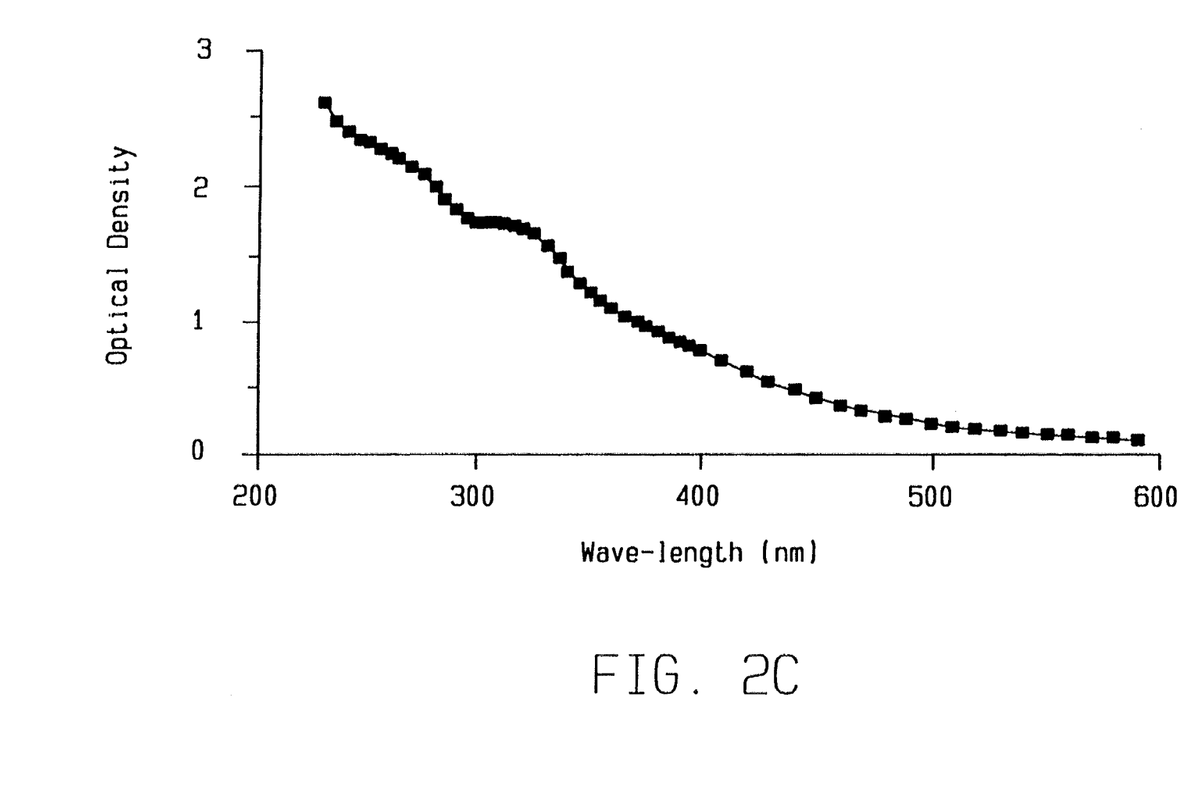
Figure 2D:
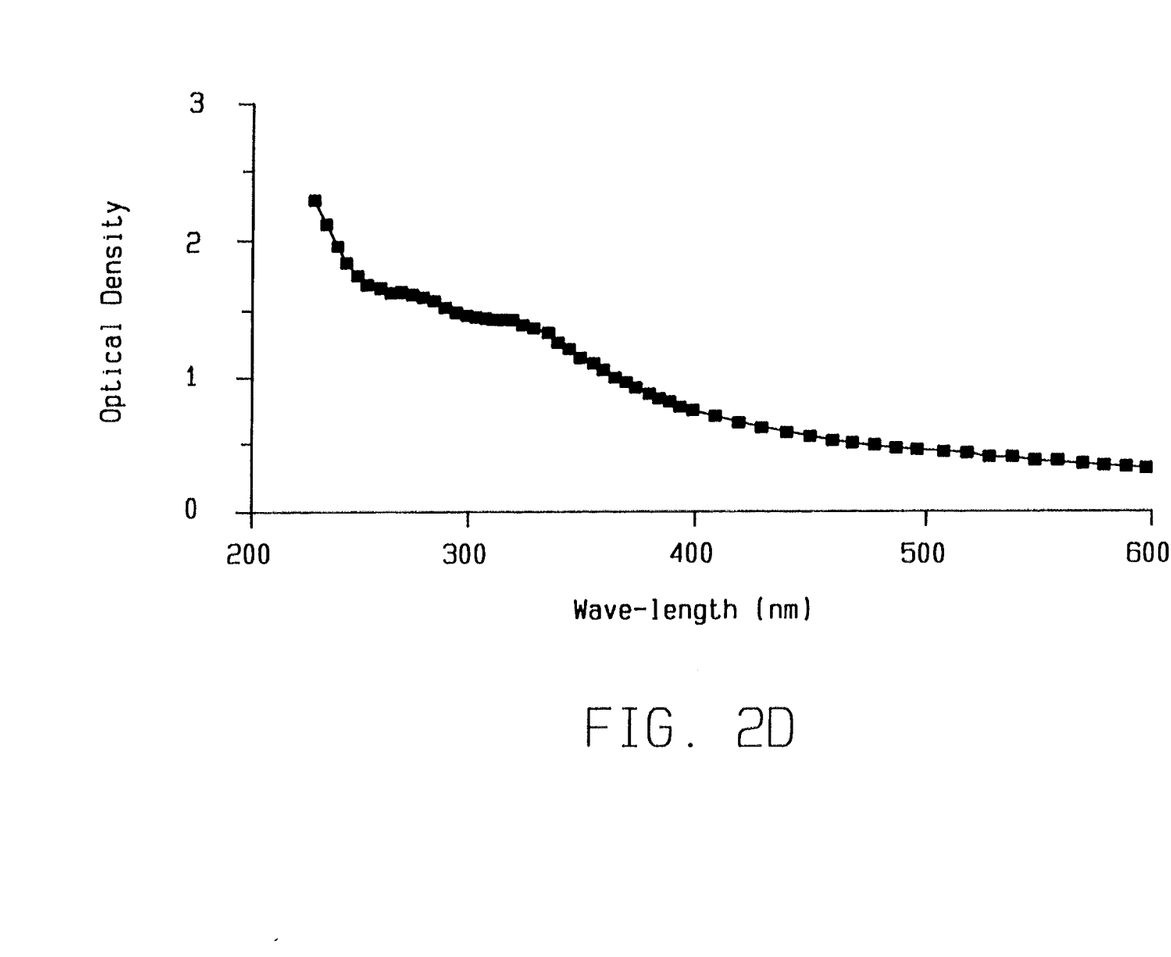

FIG. 2A-C depicts graphs showing spectral analyses of DHICA (5 mM) incubated with oxygenation for various time periods in sodium phosphate buffer (0.1M, pH 7.8, 20° C.), compared to that of the product of the dopachrome tautomerase reaction (incubation of enzyme+dopachrome 5 mM) (2D). (A=15 min; B=48 hrs; C=96 hrs). It is concluded that non-enzymatically synthesized "DHICA-melanin" (FIG. 2C) displays a similar spectrum to that of enzymatically-synthesized melanin (FIG. 2D). The graphs also demonstrate that the melanins absorb light throughout the ultraviolet and visible spectra, thus fulfilling necessary requirements for efficacy as sunscreens and UV-protectants.

Figure 3A:
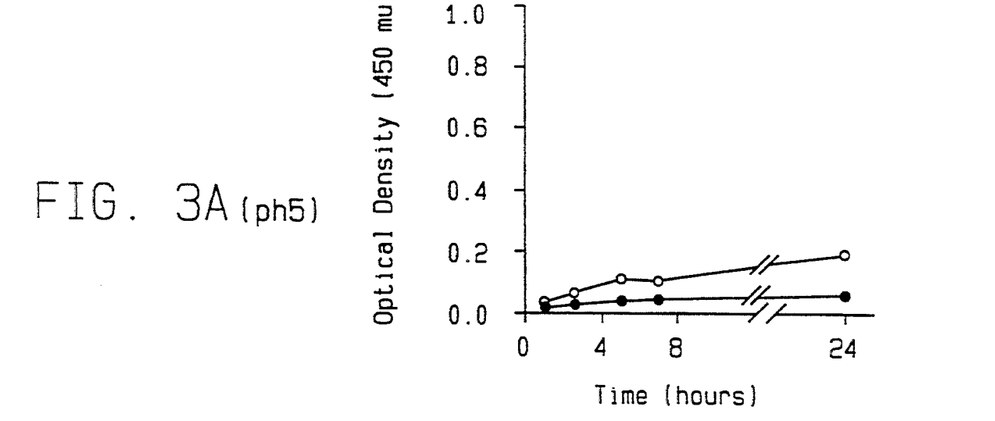
FIG. 3 depicts graphs showing the formation of melanins by incubating DHICA alone ( — ), or DHICA+DHI (○——○) at various pH's.
Figure 3B:
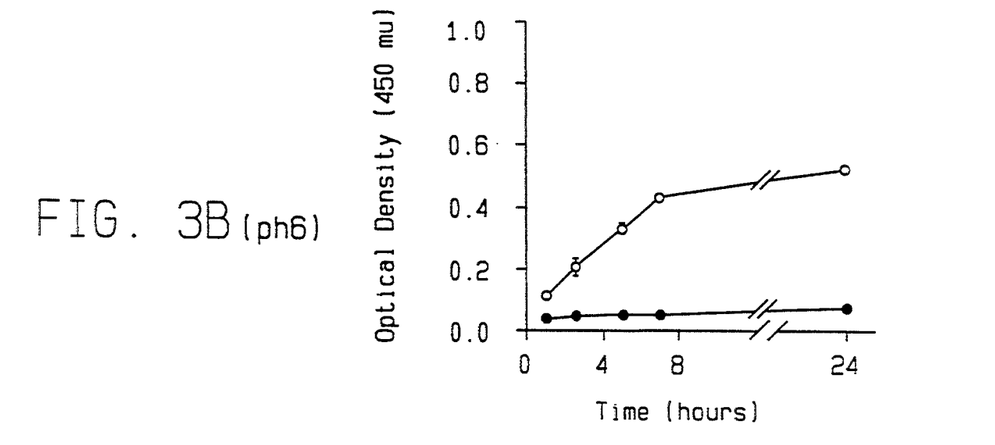
Figure 3C:
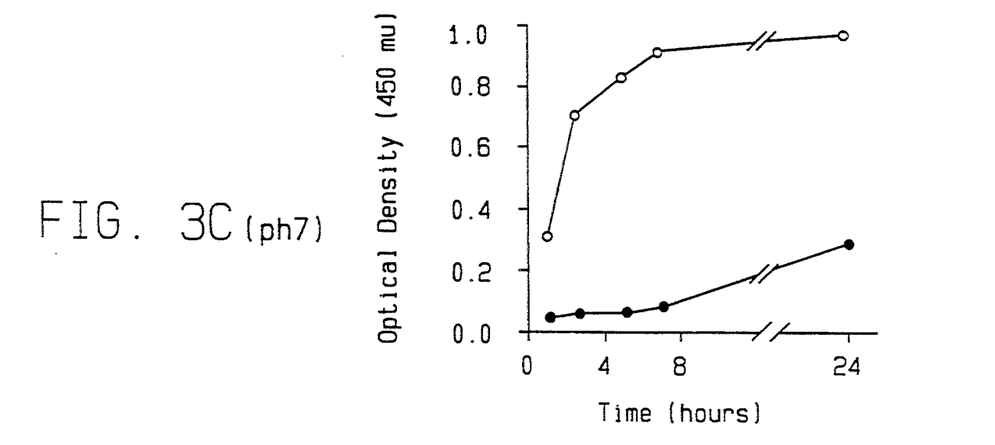

FIG. 3 depicts graphs showing the formation of melanins by incubating DHICA alone ( — ), or DHICA+DHI (○——○) at various pH's. The compounds were incubated at concentrations of 5 mM at pH 5 (sodium acetate, 0.1M), pH 6 (sodium phosphate, 0.1M), and pH 7 (sodium phosphate, 0.1M) with oxygenation, and optical densities of aliquots (1:50 dilution) were determined over 24 hours. Results for DHI alone are not shown, since this material formed a precipitate which could not be accurately quantitated by spectral analysis. When DHICA and DHI were incubated together, the rate and extent of soluble melanin formation was markedly enhanced over that achieved with DHICA alone, indicating preferential co-polymerization of DHICA and DHI (see Table 1 for quantitation of these data before and after filtration of the melanin). The results demonstrate that the polymerization reaction is enhanced as the pH is raised. Advantageously, 3-amino-tyrosine can be included in the reactions and will co-polymerize with DHICA and/or DHI.

Table 1 depicts quantitation of melanins before and after filtration through 0.22 micron filters. Results are from the same experiment shown in FIG. 3 at pH 7.

TABLE 1

| | Filtration of Melanins Synthesized from DHICA and/or DHI* | |
|---|---|---|
| | Optical Density (450µ) | |
| Precursor | − Filtration | + Filtration |
| DHICA | .341 | .351 |
| DHI | .285 | .035 |
| DHICA + DHI | 1.190 | .999 |

*DHI (5 mM) and DHICA (5 mM) were mixed vigorously, separately or together, in 0.1 M sodium phosphate pH 7.0 for 24 hours at room temperature. Aliquots were filtered, samples were diluted 1:20 with H₂O, and optical densities were determined in a spectrophotometer.

Figure 4:
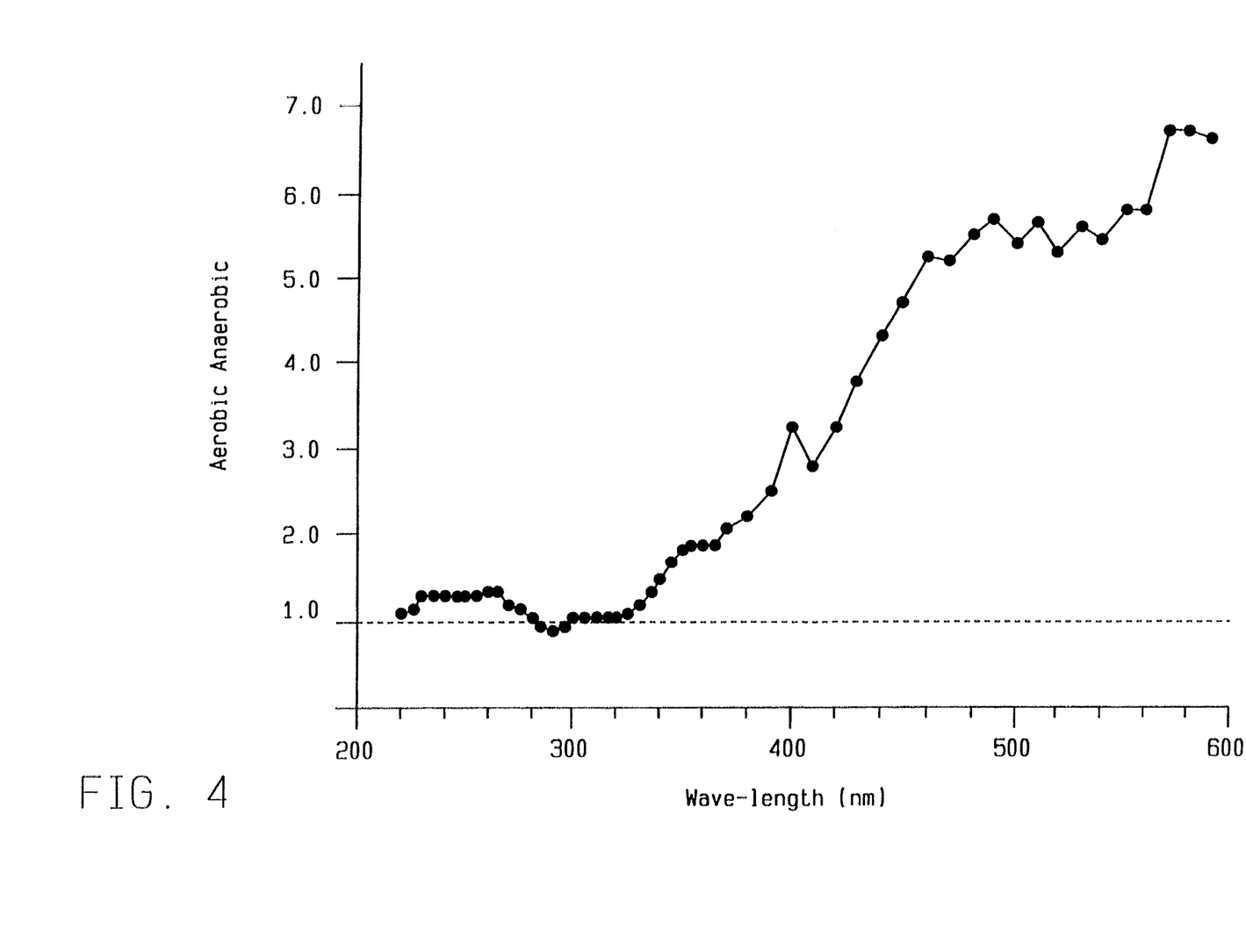
FIG. 4 depicts a graph showing the effects of aeration on the spectrum of DHICA-melanin.

FIG. 4 depicts the effects of aeration on the spectrum of DHICA-melanin. DHICA-melanin was synthesized by incubation of DHICA (5 mM) in sodium phosphate buffer (0.1M, pH 7.8) at room temperature under partial anaerobic (degassed buffers, stoppered flasks) and aerobic (gassed buffers, open flasks) conditions. After 72 hours with vigorous mixing, spectral analyses were made. The ratios of aerated/anaerobic spectra are presented. The results were that synthesis of DHICA-melanin is enhanced by aeration, and that the effects of aeration are disproportionate, being most apparent in the visible light range (above 300 nm).

Figure 5:
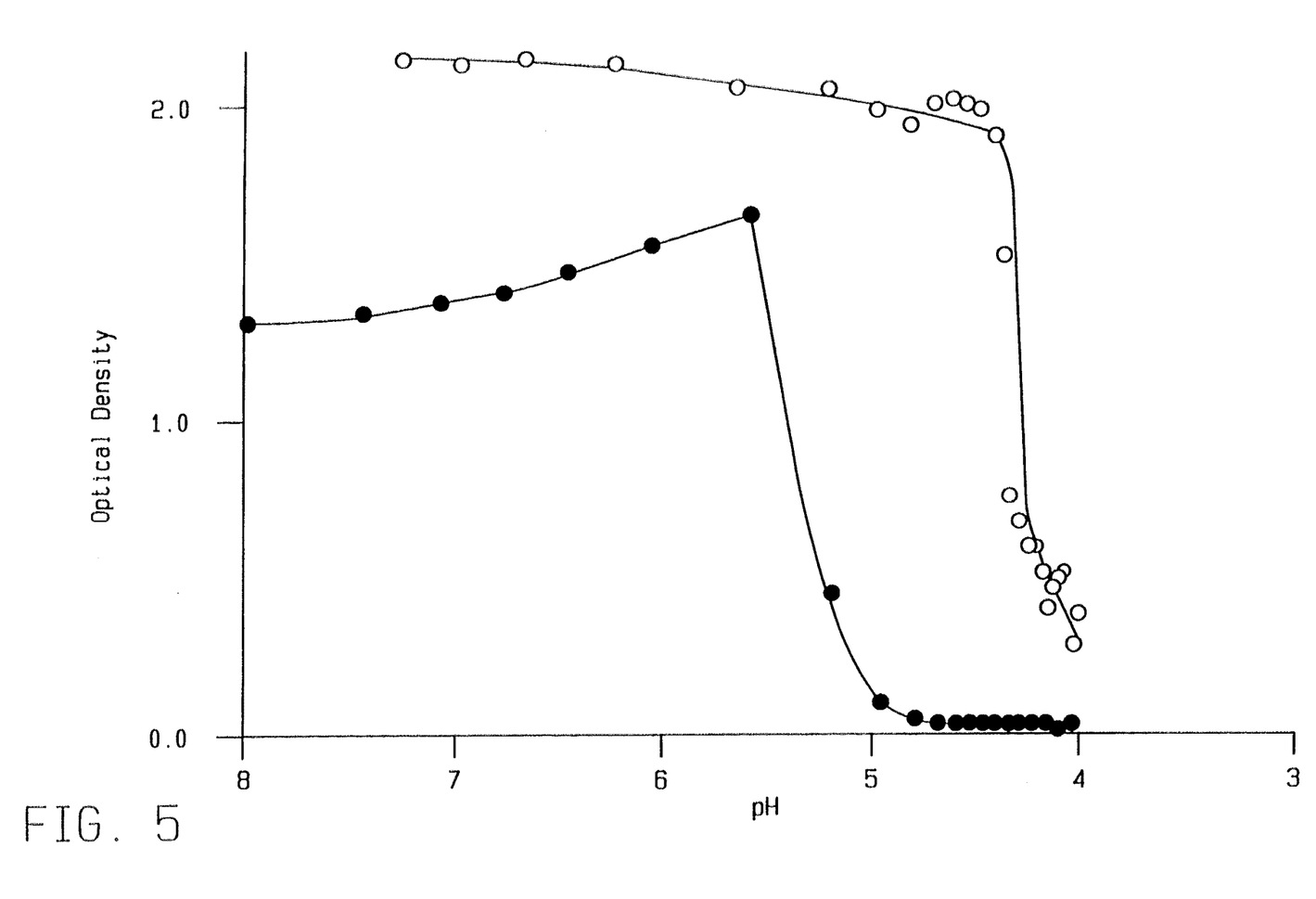
FIG. 5 depicts a graph showing the solubility of DHICA-melanin as a function of pH.

FIG. 5 depicts the solubility of DHICA-melanin as a function of pH. DHICA-melanin (○——○) or the model peptide gly:tyr ( — ) (Sigma Chemical Co., consisting of a 1:1 ratio of glutamic acid to tyrosine, average molecular weight 20,000 to 50,000 daltons) were dissolved in 0.05M sodium phosphate buffers and the pH was adjusted in separate aliquots with HCl. After 2 hours at room temperature, the aliquots were centrifuged (1000 g, 10 min), and the optical densities of the supernatant fractions were determined in a spectrophotometer at a wave length of 280 nm. The results show that both DHICA-melanins and the glu:tyr peptides are soluble around neutral pH (6-8), and precipitated at acid pH. These similarities between DHICA-melanin and the glu:tyr peptides are consistent with their common expression of carboxylic acid residues. When DHICA-melanins are precipitated at acid pH, they can readily be dissolved in organic solvents such as butanol or butoxyethanol.

Figure 6:
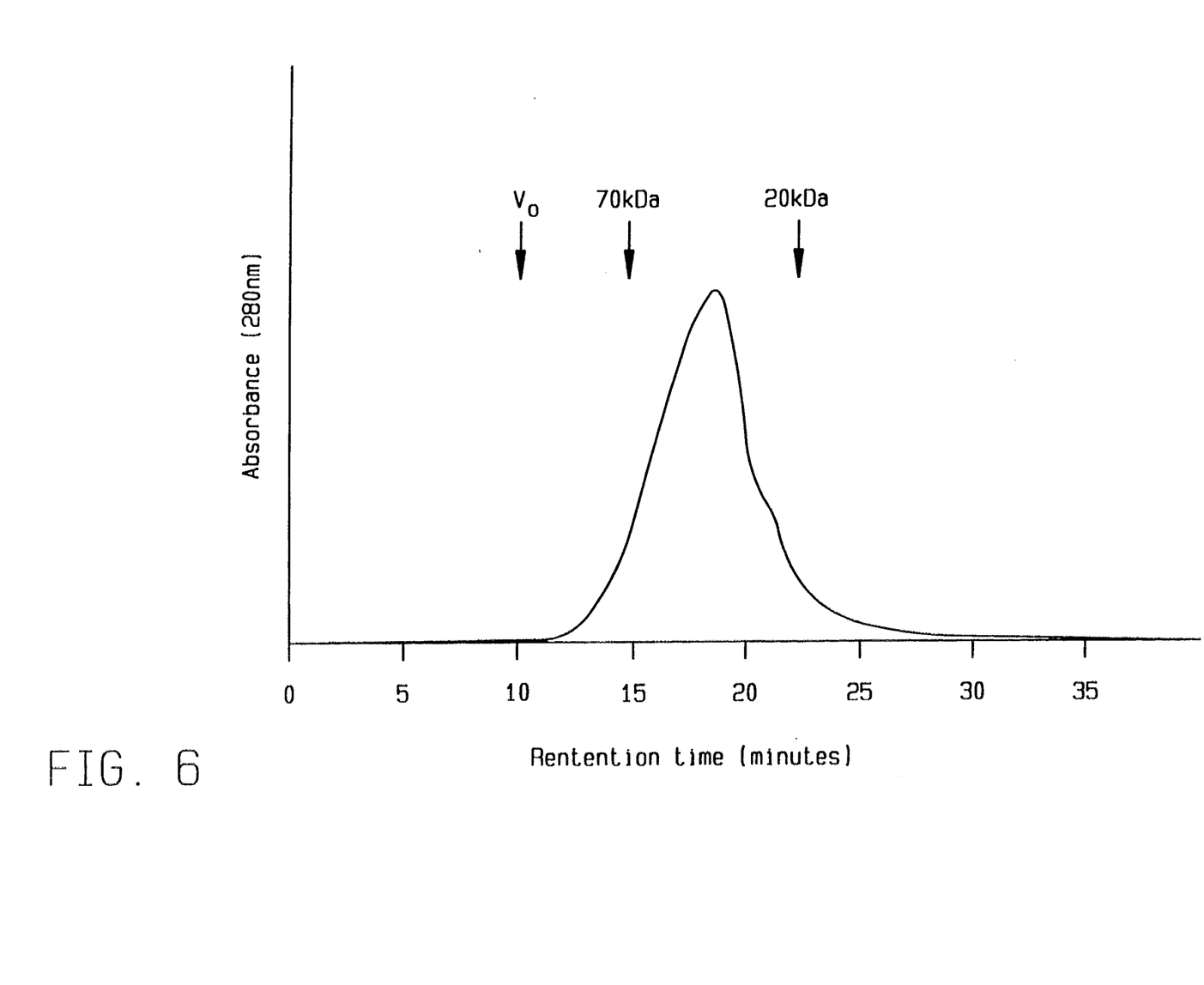
FIG. 6 depicts a graph showing chromatography of DHICA-melanin on an HPLC molecular sieve column.

FIG. 6 depicts the chromatography of DHICA-melanin on an HPLC molecular sieve column. DHICA-melanin was synthesized by incubating DHICA (5 mM) for 96 hours in sodium phosphate (0.1M, pH 7.8) with vigorous shaking in an open flask. The material was applied to a Waters Protein PAK 300 SW column and its migration rate was compared to that of known globular proteins with molecular weights of approximately 20,000 and 70,000 daltons. Results show that under the above synthetic conditions, DHICA-melanins were formed with molecular weights ranging from 20,000–70,000 daltons. However, it should be noted that molecular weights varied, depending on the synthetic conditions, and in some experiments the material eluted in the void volume of the HPLC column, corresponding to a molecular weight of greater than 200,000 daltons. Also, the HPLC column was calibrated for globular proteins, and since the secondary and tertiary structure of the DHICA-melanin has yet to be determined, the molecular weight values are estimates only.

Table 2 depicts the recovery of DHICA+DHI-melanin following dialysis and filtration. The melanin remained within dialysis tubing having a 12,000–14,000 dalton exclusion limit, and passed through a 0.22 micron filter. It was also determined that the melanin was stable to freezing/thawing, boiling, and that it could be quantitatively redissolved following lyophilization (not shown).

TABLE 2

Dialysis and Filtration of DHICA/DHI-Melanin*

| Treatment: | | |
|---|---|---|
| Dialysis | Filtration | % Starting Material |
| − | − | 100 ± 2 |
| + | − | 103 ± 9 |
| − | + | 101 ± 11 |
| + | + | 102 ± 8 |

*DHICA and DHI were mixed vigorously at 20° C. for 48 hours at a molar ratio of 1.2:1.0 (DHICA:DHI) and a total precursor concentration of 10 mM in 0.1 M sodium phosphate, pH 7.4. Following storage for approximately 8 weeks at room temperature, aliquots of the material were subjected to exhaustive dialysis in standard dialysis tubing (12,000–14,000 dalton exclusion limit) and/or filtration through 0.22μ filters. The material which remained within the dialysis tubing and/or which passed through the filters was quantitated for optical density at 450 nm and the data were normalized to the % of starting material. Results represent average ± range of duplicate samples.

FIG. 7 depicts the spectral characteristics of soluble melanin composed of a mixture of DHICA (10%) and 3-amino-tyrosine (90%). The melanin was treated with dihydroxyacetone or acetic anhydride as noted in the graph. It can be seen that both treatments produced a more even absorbance of the melanin throughout the spectrum, specifically reducing the spectral peak exhibited by untreated melanin at approximately 340 nm. Treatment of the melanin with dihydroxyacetone advantageously enhances adherence of the melanin to mammalian skin.

The invention will now be described with reference to the following non-limiting examples.

Example 1: Source of Enzymes

The enzyme preparation for the synthesis of DHICA-containing melanins can be obtained from any biological source expressing dopachrome tautomerase activity. Such activity has been described in a number of mammals, including humans, as well as in insects (Pawelek, J. M. "After Dopachrome?", Pigment Cell Research 4:53–62, 1991; Sugumaran, M. "Molecular Mechanisms for Mammalian Melanogenesis-Comparison with Insect Cuticular Sclerotization" FEBS Letters 293:4–10, 1991; Li, J. and Nappi, A. J. "Electrochemical Identification of Dopachrome Isomerase in Drosophila Melanogaster", Biochem. Biophys. Res. Comm. 180:724–729, 1991). Although in insects, the enzymatic activity ultimately results in the production of DHI rather than DHICA, which would not be useful for the production of DHICA melanin. In contrast, the mammalian reaction product of a mixture of dopachrome tautomerase and dopachrome has been confirmed from a number of studies to be DHICA (FIG. 1).

Example 2: Enzymatic Synthesis of DHICA-melanins

In a suitable reaction vessel, mix an active preparation of dopachrome tautomerase, obtained, for example, from an extract of cultured mouse melanocytes, with 5 mM dopachrome, in an aqueous buffer of 0.1M sodium phosphate, pH 6.8, at 15°–37° C. Orange dopachrome is tautomerized to colorless DHICA within one hour. Upon further incubation with ample aeration (FIG. 4), DHICA-melanin forms through auto-polymerization of DHICA (FIG. 2D). Alternatively, DHICA (5 mM) is incubated under aeration together with DHI (5 mM), 3-amino-tyrosine (5 mM), or cysteine (5 mM), either alone or in various combinations, and they, too, are then polymerized along with DHICA into melanin. In addition, following the formation of DHICA through the tautomerase reaction, hydrogen peroxide (50 mM) and/or metal ions such as $Cu^{++}$ or $Fe^{++}$ (1 mM) can be added to increase the rate of the reaction and thereby reduce the time involved for melanin formation. $H_2O_2$ and/or metal ions can be added together with DHICA and/or with DHICA in various combinations with DHI, 3-amino-tyrosine, or cysteine as mentioned above. The melanin so produced can be passed through at least a 0.45 micron filter (Tables 1 and 2), is precipitated below pH 4 (FIG. 5), is non-dialyzeable (Table 2), is of a molecular weight of greater than at least 10,000 daltons and more closely of the order of 20,000 to 70,000 daltons (FIG. 6), and is stable to freezing, thawing, and boiling.

Example 3: Non-enzymatic Synthesis of DHICA-melanins

DHICA (10 mM) is incubated in 0.2M ammonium hydroxide with aeration at 15°–70° C. for 72 hours. DHICA-melanin is formed through auto-polymerization of DHICA (FIG. 2A-C). Other suitable precursors and procedures for speeding up the reaction, as described in Example 2, can be employed. Characteristics of the non-enzymatically synthesized melanins are identical to those of enzymatically synthesized melanins (Example 2).

Example 4: Method for Adherence of DHICA-melanins to Human Skin and Hair

DHICA-melanin is mixed with any commercially available preparation of dihydroxyacetone, e.g., Lancome's Conque le du Sol oil ® to a final concentration of 1 to 5% (wt/vol) and applied evenly to the skin until the desired degree of darkening is achieved. The melanin adheres to the skin and, at suitable concentrations, masks or alters the net coloring-effects of dihydroxyacetone known to the art. Similar procedures can be followed for adherence of melanin to hair. Alternatively, DHA (5–50 mM) can be included in the synthetic reactions described in Example 2 and the melanin so produced exhibits adherence to skin and hair.

Example 5: Methods for Altering the Spectral Characteristics of DHICA-melanins

DHICA-melanin (10% wt/vol), preferably containing co-polymerized monomers of 3-amino-tyrosine, as described in Example 2, is mixed with equimolar dihydroxyacetone at room temperature, or equimolar acetic anhydride on ice for one hour. The amount of dihydroxyacetone or acetic anhydride, though preferably in equimolar concentrations, depends upon the degree of spectral alteration desired and can be increased as much as 10 fold in molar excess (see FIG. 7).

Example 6: Adaptation of DHICA-melanin to Solubility in Organic Solvents

DHICA-melanin (10% wt/vol) is precipitated from aqueous solution by lowering the pH below 4 with acid such as HCl or acetic acid (FIG. 5). The precipitated material is dried by either air-drying, lyophilization, or ether extraction. The dried melanin is then dissolved in either butanol or butoxyethanol at concentrations in the range of but not limited to 0.05–5% by volume of the organic solvent.

Example 7: Coloring Beer with DHICA-melanin

DHICA-melanin (10% wt/vol), preferably containing co-polymerized monomers of 3-amino-tyrosine, is mixed with, for example, Budweiser Beer, until a desired color is achieved. The melanin concentrations vary between, but are not limited to 0.005–1.0% by weight of the beer solution.

It will be appreciated that the instant specification and claims are set forth by way of illustration and not limitation, and that various modifications and changes may be made without departing from the spirit and scope of the present invention.

What is claimed is:

1. A composition for a sun screen for hair or skin or for providing a naturally-appearing tan to mammalian skin comprising a soluble melanin in admixture with a physiologically acceptable carrier, the soluble melanin having been produced by polymerizing a dihydroxyindole-carboxylic acid in an aqueous reaction medium in the presence of a 3 amino-tyrosine compound.

2. A method of providing a naturally-appearing tan to mammalian skin and thereby protecting against the effects of exposure to sun, comprising administering to a mammal a tan-producing amount of a soluble melanin, either alone, or in admixture with a physiologically acceptable carrier, the soluble melanin having been produced by polymerizing a dihydroxyindole-carboxylic acid in an aqueous reaction medium in the presence of a 3-amino tyrosine compound.

3. A method of providing a sunscreen for mammalian hair comprising, applying to the hair of a mammal, a sunscreening-amount of a soluble melanin either alone or in admixture with a physiologically acceptable carrier, the soluble melanin having been produced by polymerizing a dihydroxyindole-carboxylic acid in an aqueous reaction medium in the presence of a 3-amino tyrosine compound.

4. The composition according to claim 1, further comprising dihydroxyacetone.

* * * * *